(12) United States Patent
Mohanty et al.

(10) Patent No.: US 9,505,901 B2
(45) Date of Patent: Nov. 29, 2016

(54) DEPOLYMERIZATION PROCESSES, APPARATUSES AND CATALYSTS FOR USE IN CONNECTION THEREWITH

(76) Inventors: Pravansu S. Mohanty, Farmington Hills, MI (US); Swaminathan Ramesh, Farmington Hills, MI (US)

( * ) Notice: Subject to any disclaimer, the term of this patent is extended or adjusted under 35 U.S.C. 154(b) by 288 days.

(21) Appl. No.: 13/992,617
(22) PCT Filed: Dec. 8, 2011
(86) PCT No.: PCT/US2011/063947
§ 371 (c)(1), (2), (4) Date: Aug. 15, 2013
(87) PCT Pub. No.: WO2012/078871
PCT Pub. Date: Jun. 14, 2012

(65) Prior Publication Data
US 2013/0317238 A1 Nov. 28, 2013

Related U.S. Application Data
(60) Provisional application No. 61/420,961, filed on Dec. 8, 2010.

(51) Int. Cl.
*C08J 11/16* (2006.01)
*C07C 4/22* (2006.01)
(Continued)

(52) U.S. Cl.
CPC .............. *C08J 11/16* (2013.01); *B01J 8/003* (2013.01); *B01J 8/087* (2013.01); *B01J 8/10* (2013.01); *B01J 19/088* (2013.01); *B01J 19/12* (2013.01); *C07C 4/22* (2013.01); *B01J 23/34* (2013.01); *B01J 23/466* (2013.01); *B01J 2219/00033* (2013.01); *B01J 2219/0854* (2013.01);
(Continued)

(58) Field of Classification Search
CPC ............ B01J 19/12; B01J 8/087; B01J 8/10; B01J 8/003; B01J 19/008; B01J 2219/00033; B01J 2219/0894; B01J 2219/0892; B01J 2219/0854; B01J 2219/0879; B01J 23/466; B01J 23/34; C08J 11/16; C07C 4/22; Y02W 30/705
See application file for complete search history.

(56) References Cited

U.S. PATENT DOCUMENTS 5,430,174 A  7/1995 Shono et al.
6,184,427 B1  2/2001 Klepfer et al.
(Continued)

FOREIGN PATENT DOCUMENTS

CN  1850585 A  10/2006
CN  103897718 A * 7/2014
(Continued)

OTHER PUBLICATIONS

Sumi et al. Microwave Synthesis, Extraction, Improvements, and Degradation in Oil Chemsitry. Journal of Oleo Science. 62(7), 443-457, 2013.*
(Continued)

*Primary Examiner* — Sanza McClendon
(74) *Attorney, Agent, or Firm* — McDonald Hopkins LLC

(57) ABSTRACT

The present disclosure generally relates to processes, apparatuses and custom catalysts designed to depolymerize a polymer. In one embodiment, the present invention relates to a de-polymerizing apparatus, catalysts and reaction schemes to obtain useful monomers including fuel products by "in situ" reactions using coupled electromagnetic induction.

46 Claims, 17 Drawing Sheets

(51) Int. Cl.
  *B01J 8/08* (2006.01)
  *B01J 8/10* (2006.01)
  *B01J 19/08* (2006.01)
  *B01J 19/12* (2006.01)
  *B01J 8/00* (2006.01)
  *B01J 23/34* (2006.01)
  *B01J 23/46* (2006.01)

(52) U.S. Cl.
  CPC . *B01J2219/0879* (2013.01); *B01J 2219/0892* (2013.01); *B01J 2219/0894* (2013.01); *Y02W 30/705* (2015.05)

(56) References Cited

U.S. PATENT DOCUMENTS

| | | | |
|---|---|---|---|
| 6,380,448 | B1 | 4/2002 | Sato et al. |
| 6,797,913 | B2 * | 9/2004 | Van Der Walt .......... A62D 3/40 204/169 |
| 7,955,508 | B2 * | 6/2011 | Allan ........................ B01J 3/008 210/749 |
| 2005/0176997 | A1 * | 8/2005 | Yada et al. .................... 562/600 |
| 2009/0304558 | A1 * | 12/2009 | Patton et al. .................. 422/148 |
| 2010/0063271 | A1 | 3/2010 | Allan et al. |
| 2010/0108567 | A1 | 5/2010 | Medoff |
| 2010/0263867 | A1 | 10/2010 | Horton et al. |

FOREIGN PATENT DOCUMENTS

| | | | |
|---|---|---|---|
| EP | 0104873 | A2 | 4/1984 |
| EP | 1138379 | B1 | 6/2004 |
| EP | 1964877 | A1 | 9/2008 |
| JP | 200189625 | A * | 4/2001 |
| JP | 2005292228 | A * | 10/2005 |
| WO | 0132306 | A1 | 5/2001 |
| WO | 2006094421 | A1 | 9/2006 |
| WO | 2009117863 | A1 | 10/2009 |

OTHER PUBLICATIONS

International Search Report for PCT/US11/63947 dated Jun. 14, 2012.
Extended European Search Report for Application EP11847559, PCT/US2011/063947, dated May 29, 2015, 7 pp., European Patent Office, Germany.
Lixin Liu et al., "Hydrolytic Depolymerization of (Poly(ethylene terephthalate) Under Microwave Irradiation," Journal of 4pplied Polymer Science, 2005, vol. 95, pp. 719-723, Wiley Periodicals, Inc., US.
Patent Examination Report No. 1 for Application AU2011338306, report issued Jan. 20, 2016, 3 pp., Australian Government/IP Australia.
Notification of First Office Action for Application CN201180067115.7, report issued Aug. 20, 2014, 14 pp., State Intellectual Property Office for People's Republic of China, China.
Notification of Second Office Action for Application CN201180067115.7, report issued Jul. 8, 2015, 14 pp., State Intellectual Property Office for People's Republic of China, China.
Notification of Third Office Action for Application CN201180067115.7, report issued Mar. 4, 2016, 13 pp., State Intellectual Property Office for People's Republic of China, China.
First Examination Report for Application NZ612977, report issued Feb. 28, 2014, 2 pp., New Zealand Intellectual Property Office, New Zealand.
Office Action Notice for Application TW100145378, report issued May 4, 2015, 28 pp., Taiwan Intellectual Property Dffice, Ministry of Economic Affairs, Taiwan.
Results of the Substantive Examination for Application VN1-2013-0211, report issued Jun. 30, 2015, 2 pp., Ministry of Science and Technology National Office of Intellectual Property, Socialist Republic of Vietnam.

* cited by examiner

DEPOLYMERIZATION PROCESSES, APPARATUSES AND CATALYSTS FOR USE IN CONNECTION THEREWITH

RELATED APPLICATION DATA

This application claims the benefit of U.S. Provisional Application No. 61/420,961, filed on Dec. 8, 2010 and entitled "Customized Catalysts and Application Apparatus for Depolymerization Reactions," the entire disclosure of which is incorporated herein by reference.

FIELD OF THE INVENTION

The present disclosure generally relates to processes, apparatuses and custom catalysts designed to depolymerize a polymer. In one embodiment, the present invention relates to a de-polymerizing apparatus, catalysts and reaction schemes to obtain useful monomers including fuel products by "in situ" reactions using coupled electromagnetic induction.

BACKGROUND OF THE INVENTION

Addition polymers (in contrast to condensation polymers) can be depolymerized by heat to simpler monomers and its oligomers. Use of one or more catalysts can result in lower reaction temperatures at which the depolymerization reaction occurs, as well as provide some amount of control on the depolymerized product mixture. However, the product mix will always contain large quantities of unsaturated compounds that will affect its stability on exposure to air. Also, without further purification steps such as one or more fractionations, the depolymerized reaction product cannot be used directly.

Various plastics are examples of compounds produced by addition polymerization reactions. Typically, such plastics are produced from non-renewable petroleum resources and are often non-biodegradable. In the United States, such plastics like polyethylene (PE), polypropylene (PP), polyvinyl chloride (PVC) and polystyrene (PS) are produced in amounts exceeding 115,000 million pounds annually. Plastics are used in many industries to form products for sale in both industrial and residential markets. In industrial markets, these polymers are used to form packaging, insulation, construction products, and the like. In residential markets, these polymers are used to form bottles, containers, and the like.

Catalytic depolymerization of high and low density polyethylene, polypropylene and polystyrene into diesel like fuel is well known in the literature, both published and patented. Usability of such fuel is hampered by the fact that the presence of large amounts of unsaturated products reduces the stability (formation of brown polymer products) of the diesel fuel produced thereby and, as such, necessitates the need for a separate hydrogenation step to improve the stability and calorific value of the diesel so produced.

Accordingly, the depolymerization of polymers requires a careful selection of catalysts, processing as well as separation scheme to extract valuable diesel like fuel. FIG. 1 presents a gas chromatograph illustrating the identity and relative quantities of various monomers formed from pyrolysis of polyethylene and polypropylene. The monomers include alkanes, alkenes, and alkynes or dienes having from 2 to 40 carbon atoms wherein the alkanes are colored green, the alkenes are colored red, and the alkynes and dienes are colored blue.

Besides the addition polymers, there are condensation polymers, which include polyesters (PET), polyurethanes (PU), nylons or polyimides and the like. There are also thermoset polymers (example automotive coatings), which are three dimensional polymer networks formed by cross-linking reactions of the linear polymers.

In contrast to polyethylene, polypropylene and other polyenes, condensation polymers and thermosets cannot be "depolymerized" using thermal energy. Instead, one must rely on extensive chemical reactions to convert such products back to their starting materials and, as such, this is economically prohibitive to perform.

Given the above, only a small fraction of the polymers produced are recycled and re-used. Polymers that are not recycled and re-used present potential environmental pollution risks when discarded, are not utilized for energy or raw materials, and contribute to an increased reliance on non-renewable petroleum resources.

SUMMARY OF THE INVENTION

The present disclosure generally relates to processes, apparatuses and specially designed catalysts designed to depolymerize a polymer. In one embodiment, the present invention relates to a de-polymerizing apparatus, catalysts and reaction schemes to obtain useful monomers including fuel products by "in situ" reactions using coupled electromagnetic induction.

This present disclosure provides for apparatus, reaction schemes and reaction conditions comprising the use of coupled electromagnetic induction and customized catalyst materials to depolymerize all kinds of polymers to useful monomers including fuel type mixtures. The method offers unique advantages in terms of product selectivity and process efficiency.

Further, in one embodiment the methods of the present invention form, under certain conditions, high purity monomers that may be used as starting materials for highly value added functional monomers. In one embodiment, these functional monomers can be formed in situ in the reactor thus making the process economical.

In another embodiment, the method of the present invention includes the step of introducing a polymer into a reactor, and depolymerizing the polymer in the vessel while in the presence of at least one catalyst. As will be discussed below, the methods of the present invention can, in one embodiment, utilize one or more customized catalyst designed to facilitate in situ depolymerization reactions.

In one embodiment, the present invention relates to a method of depolymerizing polymers, the method comprising the steps of: (i) providing one or more polymer starting materials, or feed materials; (ii) providing a reactor to depolymerize the one or more polymer starting materials, or feed materials, into one or more monomers: (iii) heating the one or more polymer starting materials, or feed materials, at a rate of from about 10° C./second to about 1000° C./second; and (iv) providing an electromagnetic induction field to facilitate the depolymerization of the one or more polymer starting materials, or feed materials, into their constituent monomers, wherein the method utilizes one or more catalysts that permit in situ reactions to yield one or more functional monomers.

In another embodiment, the present invention relates to a method of depolymerizing polymers, the method comprising the steps of: (a) providing one or more polymer starting materials, or feed materials; (b) providing a reactor to depolymerize the one or more polymer starting materials, or feed materials, into one or more monomers; (c) heating the one or more polymer starting materials, or feed materials, at a rate of from about 10° C./second to about 1000° C./second; (d) providing an electromagnetic induction field to facilitate the depolymerization of the one or more polymer starting materials, or feed materials, into their constituent monomers; and (e) selectively harvesting at least one of the monomers produced by the method or converting at least one of the monomers into one or more stable value added products, wherein the method utilizes one or more catalysts that permit in situ reactions to yield one or more functional monomers.

In still another embodiment, the present invention relates to a method of depolymerizing polymers, the method comprising the steps of: (I) providing a polymer starting material, or feed material; (II) providing a reactor to depolymerize the polymer starting material, or feed material, into a constituent monomer; (III) heating the one or more polymer starting materials, or feed materials, at a rate of from about 10° C./second to about 1000° C./second; and (IV) providing an electromagnetic induction field to facilitate the depolymerization of the material, or feed material into its constituent monomer, wherein the method achieves a yield of constituent monomer of at least about 80 weight percent based on the extractable weight percent value contained in the polymer starting material, or feed material, subjected to depolymerization.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure. For purposes of clarity, not every component is labeled in every figure, nor is every component of each embodiment of the disclosure shown.

DESCRIPTION OF THE INVENTION

The present disclosure generally relates to processes, apparatuses and specially designed catalysts designed to depolymerize a polymer. In one embodiment, the present invention relates to a de-polymerizing apparatus, catalysts and reaction schemes to obtain useful monomers including fuel products by "in situ" reactions using coupled electromagnetic induction.

Non-limiting embodiments of the present disclosure will be described by way of example with reference to the accompanying Figures, which are schematic and are not intended to be drawn to scale.

Figure 2:
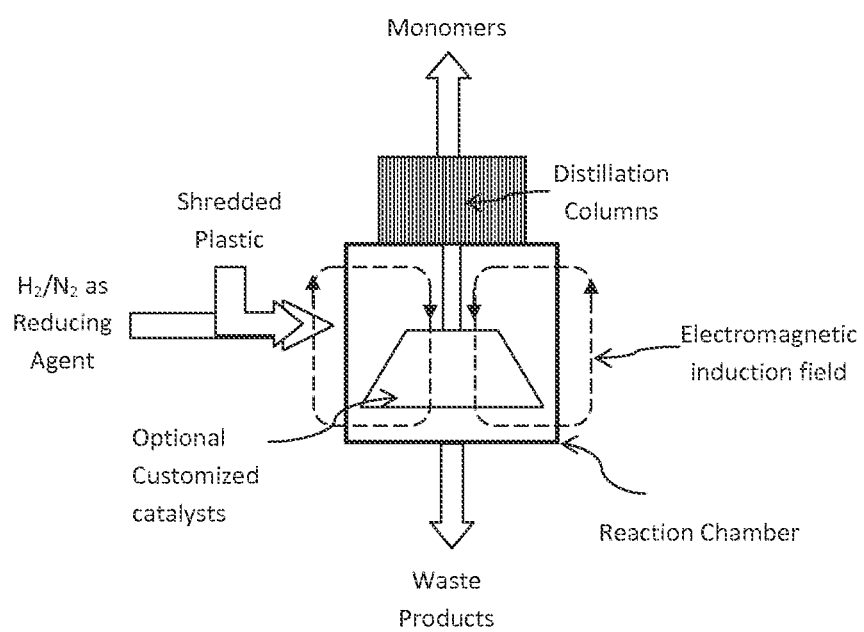
FIG. 2 is a block diagram illustrating an embodiment of the present invention comprising a feeder, a reactor with coupled electromagnetic induction field and optional customized catalysts through which $H_2$ and $N_2$ gasses as the reducing agents, and a distillation columns and the depolymerized polymer flow, showing recycling of the polymers and formation of monomers.

Referring initially to FIG. 2, the block diagram illustrates one embodiment of the present disclosure in which shredded polymers are continuously fed by a feeder into a reactor along with one or more inert gases selected from $N_2$, helium, or other inert gas to keep the atmosphere inert (the gas feed may also contain $H_2$ gas as the reducing agent if needed). The polymer starting material, or feed material, is subject to a coupled electromagnetic induction energy field resulting in fusion and depolymerization. In one instance, this embodiment can be conducted in the presence of one or more catalysts compounds that will be described in detail below. In another embodiment, the above process can be conducted in the absence of a catalyst. In both instances, the polymer compositions so treated are converted into useful functional monomers. Regarding the strength of the electromagnetic field utilized to provide the coupled electromagnetic induction energy field such a parameter will vary depending upon the amount of polymer starting material, or feed material present, the size of the reactor, the process rate, etc. Accordingly, the present invention is not limited to any one electromagnetic field strength.

The polymer feed material that can be used in conjunction with the present invention can be any thermoplastic or thermoset known in the art. In one embodiment, the polymer feed material is a polymerization product of monomers including, but not limited to, aliphatic monomers, aromatic monomers, and/or suitable combinations of any two or more thereof. In another embodiment, the polymer feed material is the polymerization product of monomers including unsaturated monomers such as alkenes and dienes having carbon-carbon double bonds, alkynes having carbon-carbon triple bonds, and styrene monomers, and/or suitable combinations of two or more thereof. As such, the polymer feed material utilized in conjunction with the present invention can include one or more polyethylenes (PE), one or more polypropylenes (PP), one or more polyvinyl chlorides (PVC), one or more polystyrenes (PS), and/or suitable combinations of any two or more thereof. In one embodiment, the polymer feed materials of the present invention have recycle codes of 2, 3, 4, 5 and 6. In still another embodiment, the polymer feed material of the present invention is a condensation polymer formed from reaction of one or more polyalcohols with one or more polycarboxy acids in the absence of water. As would be appreciated by those of skill in the art, these are polyesters and have a recycle code of 1. The polymer feed material can, in another embodiment, be one or more polyurethanes, made by reacting at least one isocyanate with at least one alcohol. The polymer feed material can also be a nylon, which is a polyimide, formed from the reaction of one or more polycarboxylic acids with one or more polyamines. It should be noted that the polymer feed material of the present invention is not limited to just the above examples. Rather, the polymer feed material of the present invention can also be selected from a myriad of other polymers formed from the reaction of two functional groups with the elimination of simple molecules (condensation), which correspond to recycling code 7. The polymer feed material of the present invention can, in one embodiment, be atactic, isotactic or syndiotactic. For non-limiting illustrative purposes only, the chemical structures of various polymers are shown below:

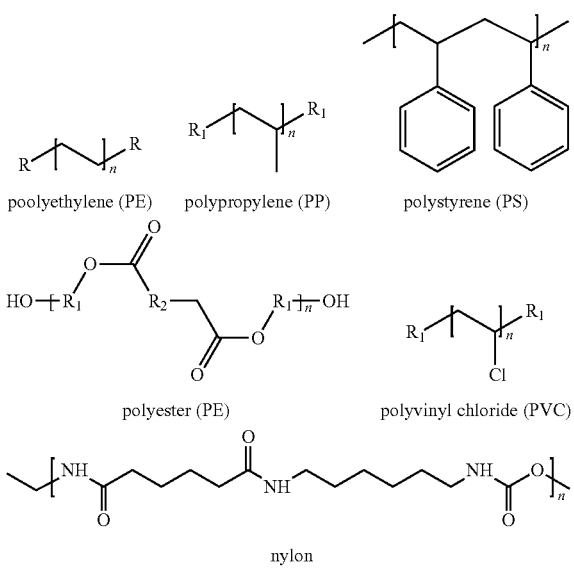

poolyethylene (PE)   polypropylene (PP)   polystyrene (PS)

polyester (PE)   polyvinyl chloride (PVC)

nylon

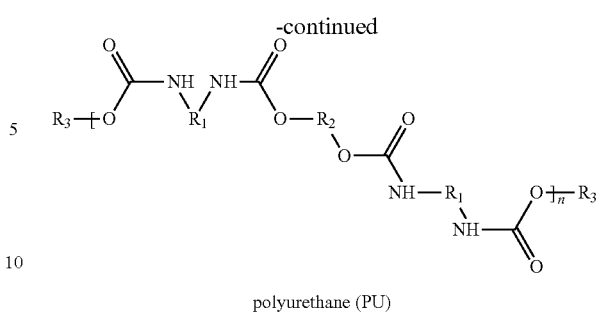

polyurethane (PU)

wherein n may be any integer equal to two or more.

The polymer feed material is typically supplied in various commercial product forms. Such forms include, but are not limited to, containers, packaging, insulation, construction products, and/or combinations of any two or more thereof. However, it is contemplated that the polymer feed material can be in any form. Such forms include, but are not limited to, any commercial product form, commercial product rejects (i.e., defective products that would otherwise be disposed of), and/or left over polymer from a manufacturing process (e.g., an extrusion process, blow molding process, etc.). In one embodiment, if so desired and/ort necessary prior to introduction of the polymer feed material into the reactor, the polymer feed material can be processed via one or more physical and/or chemical treatments to ease introduction into the reactor. If the polymer feed material is processed with one or more physical treatments, the polymer can be cleaned to remove dirt, oil, grease, detergents, food, exogenous plant and animal contaminants, and/or combinations of any two or more thereof. The polymer feed material can be cleaned with any method known to those of skill in the art. In one embodiment, the polymer feed material is cleaned using pressurized water jets, floatation, surfactants, scrubbers and the like, and/or combinations of two or more thereof. The polymer feed material can also be reduced in size through any method known in the art including, but not limited to, shredding, grinding, heating, melting, burning, smashing, dissolving, tearing, crushing, and/or combinations of two or more thereof. If reduced in size, the polymer feed material can be reduced to any size including, but not limited to, powder, nanopowder, pellets, etc. As used herein the word, or prefix, "nano" refers to any object having a size, or even just one dimension, of less than about 1,000 nanometers, less than about 750 nanometers, less than about 500 nanometers, less than about 250 nanometers, less than about 100 nanometers, less than about 50 nanometers, less than about 25 nanometers, less than about 10 nanometers, less than about 5 nanometers, or even less than about 1. Here, as well as elsewhere in the specification can claims, individual range values, or limits, can be combined to form additional and/or non-disclosed open and closed ranges. The polymer feed material can also be physically treated through stirring, mixing, sonicating, by using radio waves, magnetic energy, and light energy, and/or combinations of two or more thereof. If the polymer feed material is processed with chemical treatments, the polymer feed material can be combined with one or more catalysts, one or more enzymes, one or more fillers, one or more acids, one or more bases, one or more salts, one or more cationic and anionic compounds, one or more processing agents, and/or combinations of any two or more thereof. In one embodiment, the polymer feed material of the present invention is cleaned, shredded, and melted.

Referring now to the step of introducing the polymer feed material (or polymer material for recycling) into the reactor, the polymer feed material can be introduced into the reactor in any setting and in any amount. The polymer feed material can be introduced into the reactor in laboratories utilizing small amounts on a gram and smaller scale and in industrial recycling facilities utilizing large amounts on a kilogram to kiloton, or even larger scale. The reactor can be any vessel known in the art and can include one or more laboratory and/or industrial size vessels and reactors. In one embodiment, the method is utilized on a kilogram to kiloton (or even larger scale) scale in any suitably sized industrial recycling facility (or facilities) utilizing a suitable designed industrial size reactor, or reactors.

The reactor can be any reactor known in the art including, but not limited to, screw reactors, plug reactors, and combinations of any two or more thereof. The reactor can also be operated in any type of mode including, but not limited to, batch and continuous modes. In one embodiment, the reactor is operated in continuous mode to reduce energy consumption, operating costs, size of the reactor, running time, down time, etc. The reactor may further be operated at any temperature.

After the polymer feed material (or polymer material to be recycled and/or depolymerized) is introduced into the reactor, the method comprises the step of depolymerizing the polymer, as previously discussed above. The polymer feed material can be fragmented by any method known in the art. It is contemplated that the polymer feed material can be decomposed by heating, actinic and microwave radiation, or combinations of any two or more thereof. In one embodiment, the polymer feed material is decomposed by heating with conventional methods, with microwave radiation, with resistive heating, utilizing fossil fuels, with induction heaters, with plasma, with solar energy, with radioactive energy, or combinations of any two or more thereof. In still another embodiment, depolymerization is accomplished with at least one coupled electromagnetic induction field directly applied to the mixing device/polymers using the setup described below. When the polymer feed material is decomposed, the polymer feed material is preferably at least partially reverse polymerized (i.e., broken down) into monomers.

Figure 3:
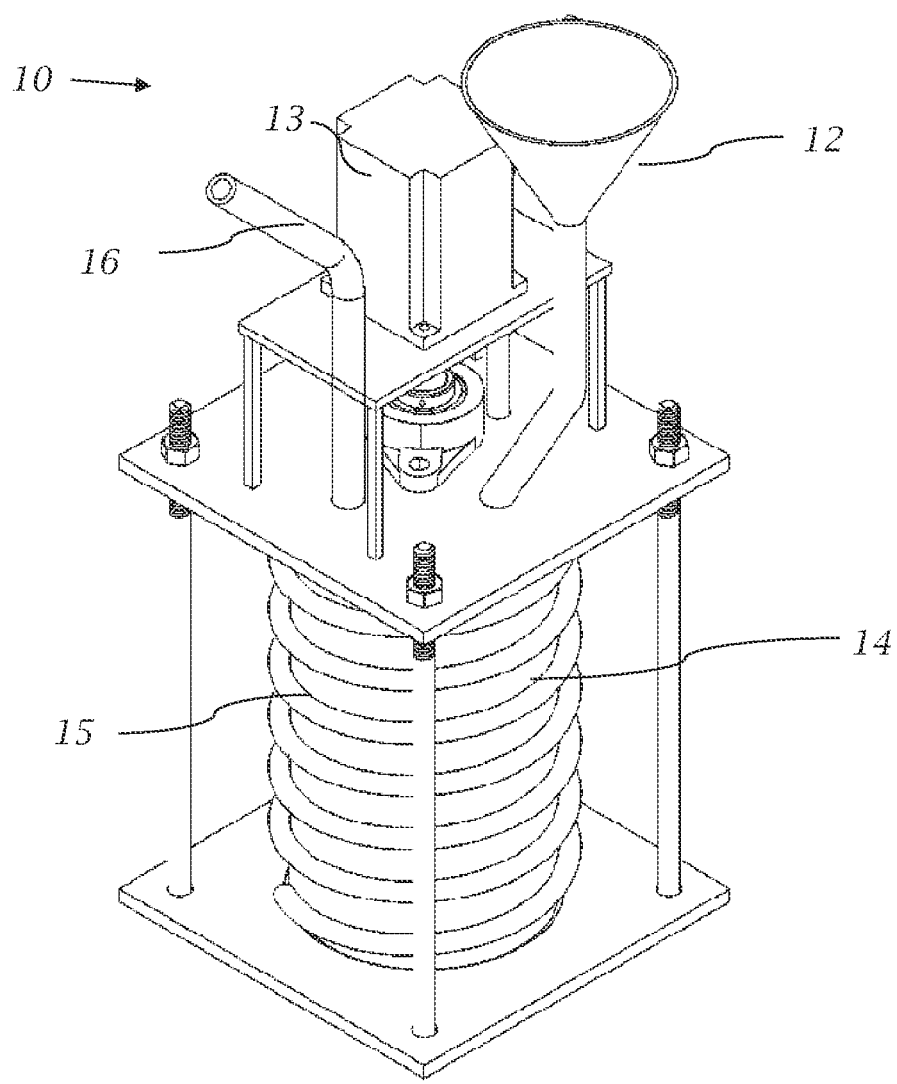
FIG. 3 is a schematic view of an exemplary embodiment of the present disclosure comprising the processing apparatus scheme of FIG. 2 with an induction coil.
Figure 4:
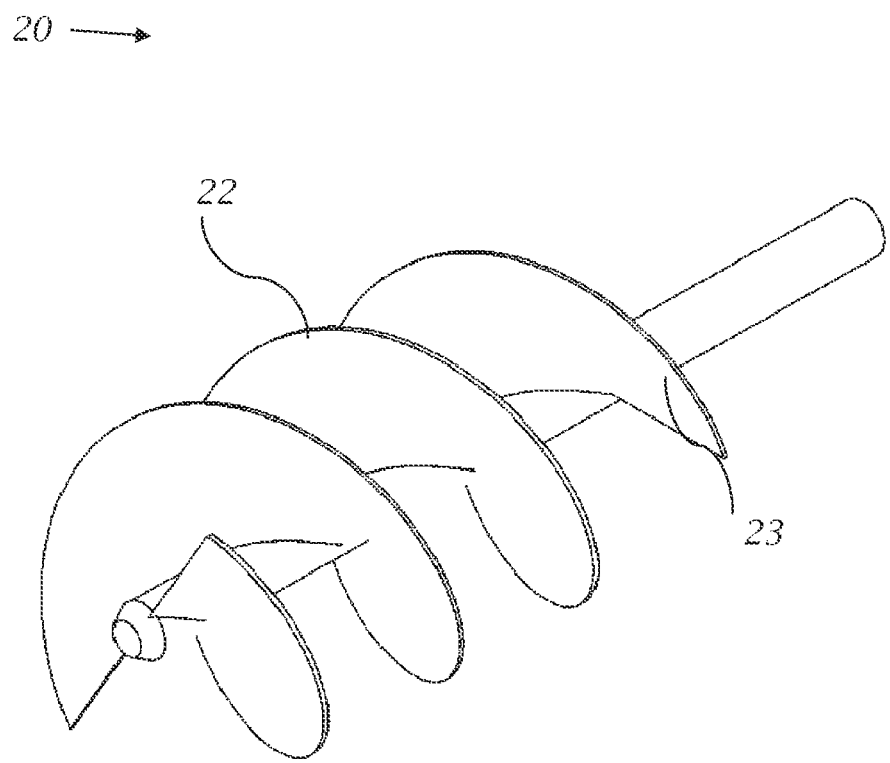
FIG. 4 is a schematic view of an exemplary embodiment of the mixing device inside the processing apparatus assembly of FIG. 3 comprising impeller blades coated with designed catalysts.

With reference to FIG. 3, in one embodiment of the present invention, an apparatus 10 for carrying out one or more methods in accordance with the disclosure contained herein comprises a feeder 12, a motor 13, a reactor 14 with internal mixing device, and condensers 16. Polymer feed material (or polymer material to be recycled and/or depolymerized) from feeder 12 is continuously fed into rector 14, whose internal mixing device couples with the electromagnetic induction field applied via induction coil 15. Referring to FIG. 4, the internal mixing device comprises of impeller assembly 20 that is designed to function with and/or facilitate the use of electromagnetic induction coupling and thus is energized upon application of induction current through coil 15. The impeller 20 mixes and heats the incoming polymer simultaneously ensuring uniform temperature in the feed material.

In one embodiment, the polymer feed material is heated. If so heated, the polymer feed material can be heated to any desired temperature. In one embodiment, the polymer feed material is heated to a temperature of from about 25° C. to about 1000° C., or from about 100° C. to about 700° C., or even from about 200° C. to about 400° C. Here, as well as elsewhere in the specification can claims, individual range values, or limits, can be combined to form additional and/or non-disclosed open and closed ranges. In another embodiment, the polymer feed material can be heated at any rate. In one embodiment, the polymer feed material is heated at a rate of from about 10° C./second to about 1000° C./second, or from about 50° C./second to about 500° C./second, or even from about 100° C./second to about 200° C./second. Here, as well as elsewhere in the specification can claims, individual range values, or limits, can be combined to form additional and/or non-disclosed open and closed ranges. With the setup described above, one can, for example, achieve a heating rate of from about 10° C./second to about 1000° C./second, or even about 200° C. per second.

Figure 1:
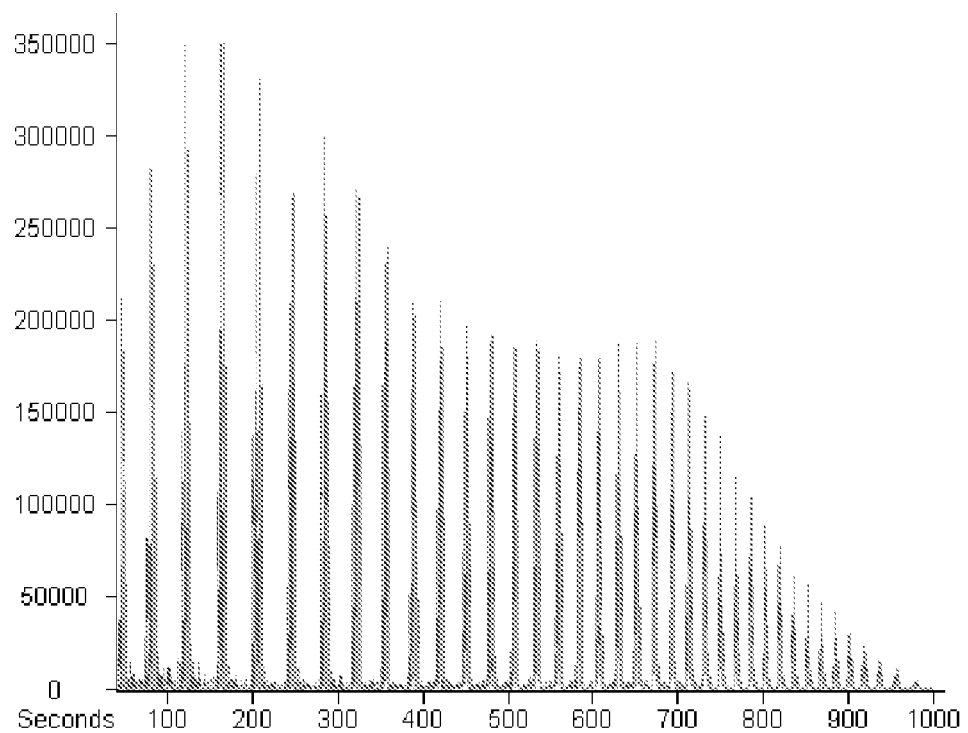
FIG. 1 is a gas chromatograph illustrating identity and relative quantities of monomers formed from pyrolysis of polyethylene and polypropylene as the exemplary polymer of the present invention.

If the polymer feed material is heated at a rate of from about 100° C. to about 1000° C./second, especially in an absence of air, the polymer is subject to pyrolysis. If the polymer feed material is heated at a rate of from about 25° C./second to 100° C./second, the polymer is subject to thermolysis. As is known in the art, pyrolysis includes rapid heating of a polymer material to at least partially reverse polymerize the polymer and form/yield monomers. Similarly, as is also known in the art, thermolysis includes the slower heating of a polymer material to at least partially reverse polymerize the polymer and form monomers. As is shown in FIG. 1, if the polymer feed material includes pyrolyzed polyethylene and/or polypropylene, alkanes, alkenes, and alkynes or dienes having between 2 and 40 carbon atoms are produced, wherein the alkanes are colored green, the alkenes are colored red, and the alkynes and dienes are colored blue. After formation, the monomers can be removed by boiling or with a stream of inert gas including, but not limited to, helium, neon, argon, krypton, xenon, nitrogen, hydrogen, or combinations of any two or more thereof.

Figure 5:
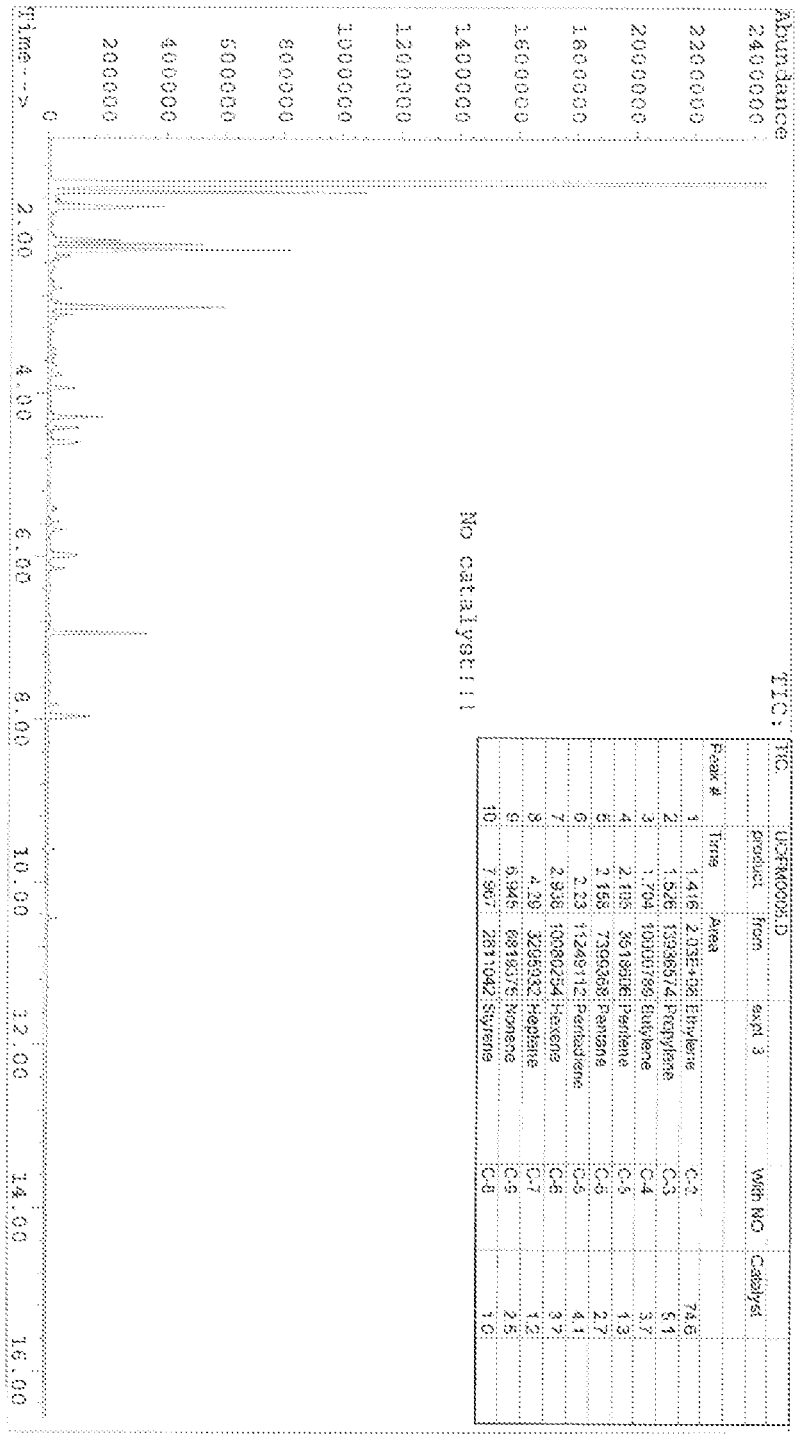
FIG. 5 is an exemplary result demonstrating selective harvesting of starting monomers, according to the principles of the present teachings.
Figure 6:
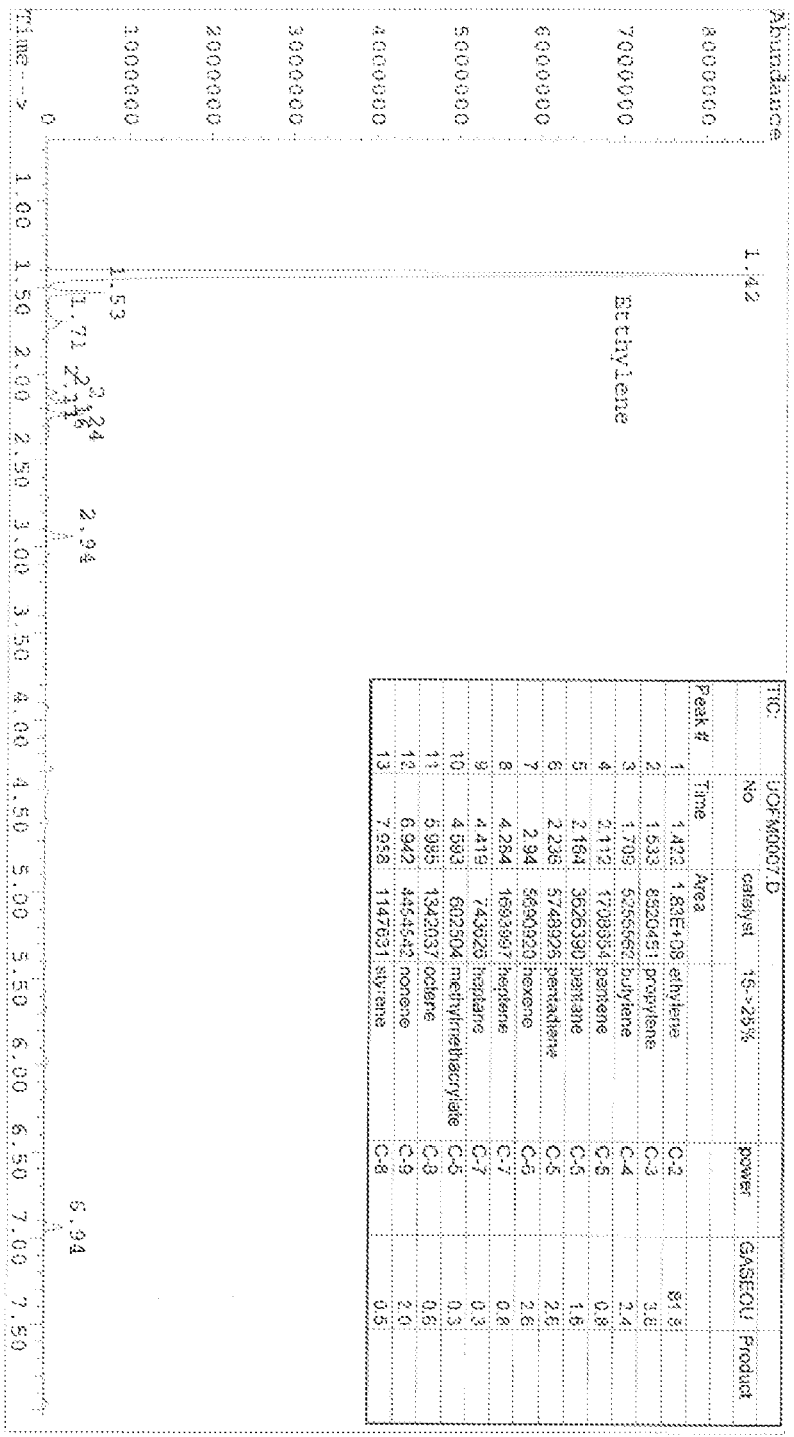
FIG. 6 is an exemplary result demonstrating selective harvesting of starting monomers in the absence of any catalysts, according to the principles of the present teachings.

When a polymer feed material is processed using the coupled electromagnetic induction setup as described herein, a different result is observed as illustrated in FIGS. 5 and 6. Instead of a varying distribution of a number of different alkenes, alkanes and dienes, the major product yielded in these circumstances is alkene monomers. This results in over about 80 percent to about 85 percent of the products produce as a gas. A few percentages of liquid and solid products are also found.

The coupled electromagnetic induction heat processing using the setup discussed herein permits one to convert a polymer to its individual base monomer while realizing both a high yield and specificity for the particular monomer that gave rise to the polymer material being depolymerized. For example, polyethylene will yield ethylene monomer at a yield rate of about 80 percent or greater. A polypropylene will yield propylene monomer at a yield rate of about 80 percent or greater. A combination of polyethylene and polypropylene will yield a mixture of ethylene and propylene monomers in the ratio of such materials in the polymer feed material at a yield rate of about 80 percent or greater. A polystyrene will yield styrene monomer at a yield rate of about 80 percent or greater. Similarly, a PVC will yield vinyl chloride monomer at a yield rate of about 80 percent or greater.

Figure 7:
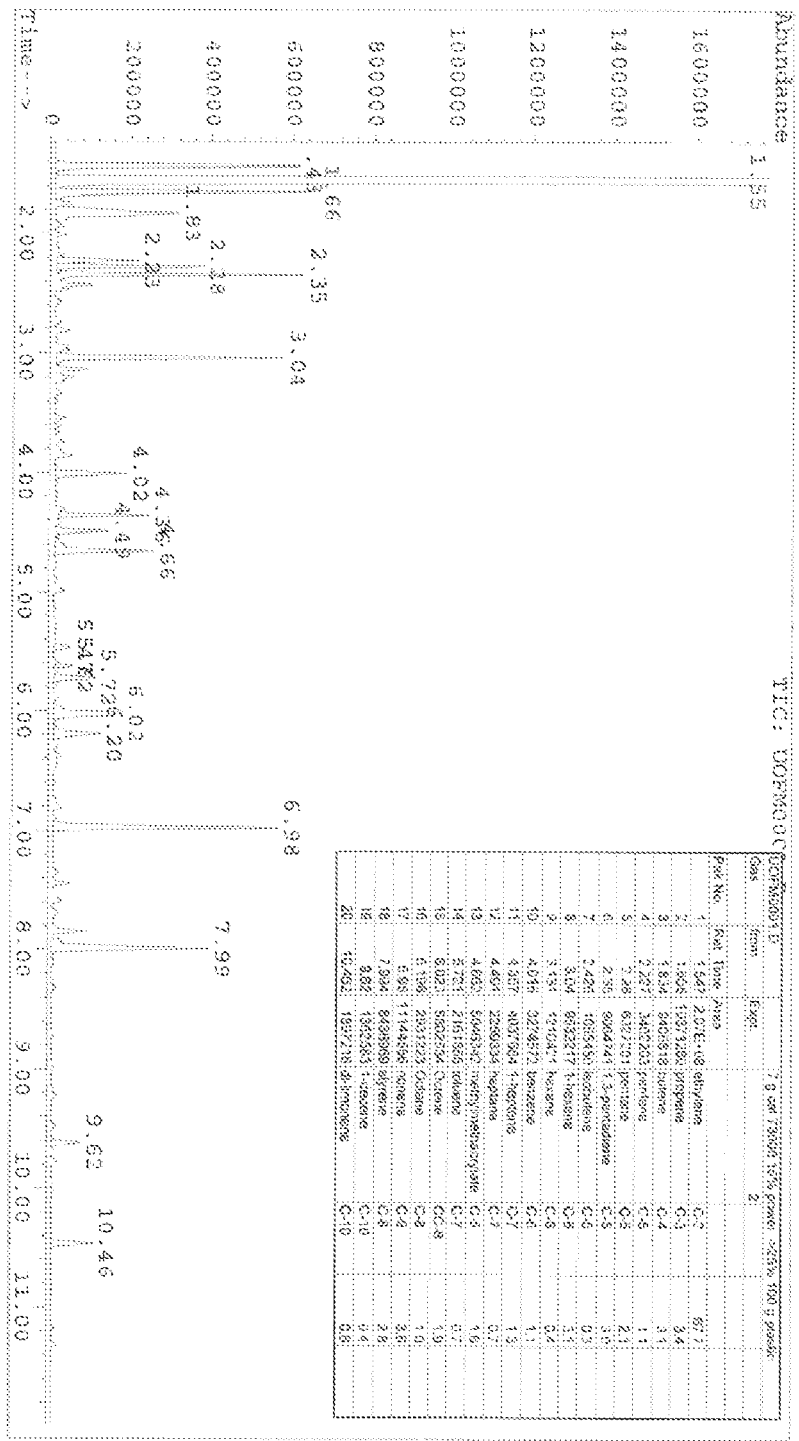
FIG. 7 is an exemplary result demonstrating harvesting of mixed monomers in the presence of catalysts, according to the principles of the present teachings.

When coupled electromagnetic induction heating is employed to depolymerize a polymer in presence of a catalyst a somewhat different behavior is observed. One still obtains a majority of the reaction products as individual monomers (see FIG. 7), but one sees more waxy solid products formed as well (see FIG. 8). While not wishing to be bound to any one theory, it is postulated that there are two different reaction pathways occurring, the catalyzed reaction tending to yield (or be more favorable towards) fuel like products. As can be seen there from, the product distribution of FIG. 8 looks similar to that of FIG. 1 which is obtained via the thermolysis of various polymers that are in the case of FIG. 8 utilized as the starting or feed material for the present invention.

products distilled off. Similar depolymerization of thermosets can be envisaged and while not wishing to be bound to any one theory or chemical mechanism, possible chemistries are depicted below:

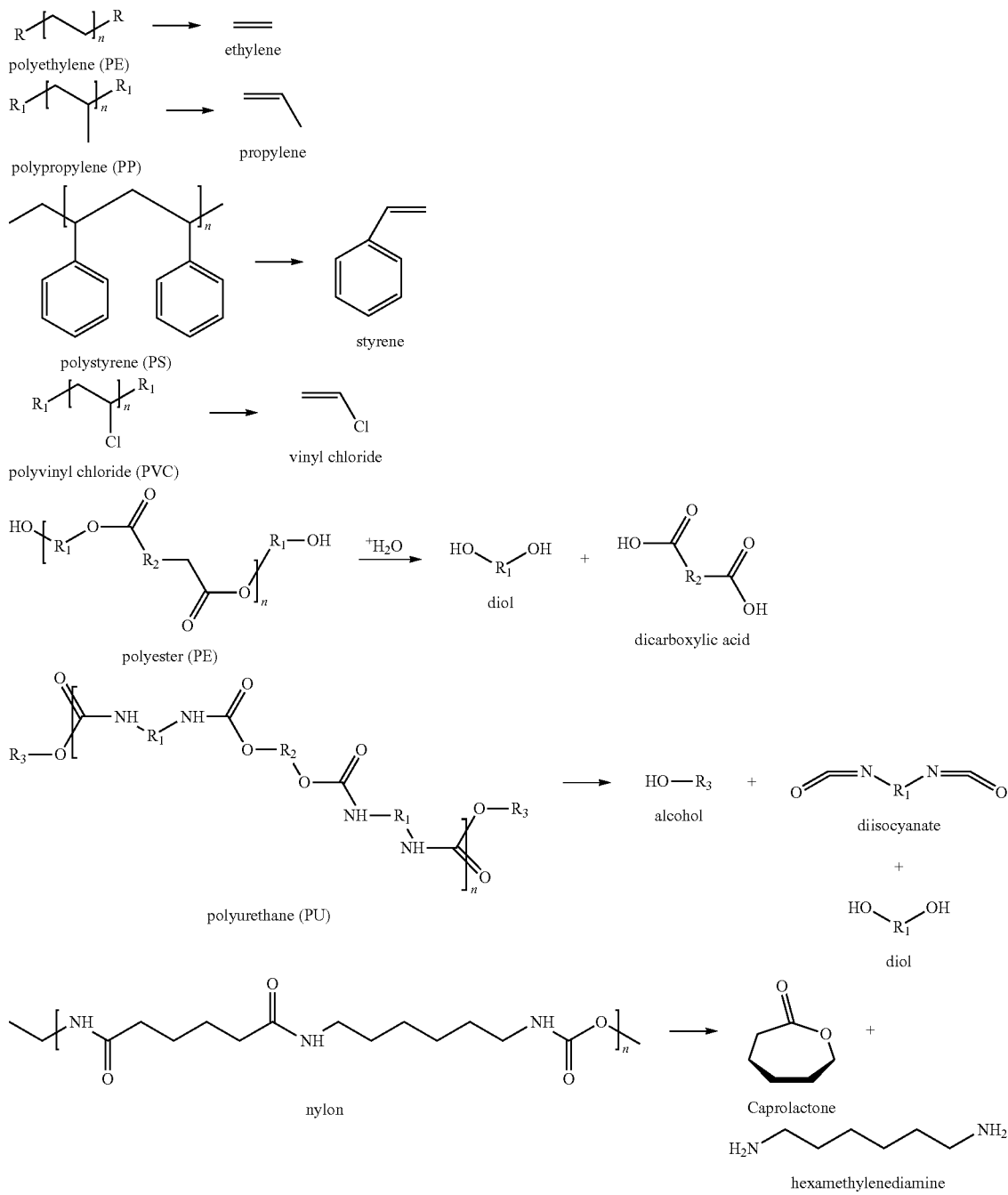

The coupled electromagnetic induction principle discussed herein permits one to depolymerize a urethane into an isocyanate (and/or polyisocyanate) and alcohol functional monomer or a polyol. By effective distillation of one of the products, each of the reactive compounds can be obtained in high yields. Similarly, a polyester will yield an anhydride of a dicarboxylic acid and a polyol if during the process enough water is introduced catalytically and the As the polymer feed material, or starting material, is depolymerized, the method of the present invention can also include the step of monitoring the formation of monomers. The monomers can be monitored online, offline, or through a combination of both online and offline monitoring. Also, the step of monitoring can include utilizing any monitoring technique known by those of skill in the art. The monitoring technique can include, but is not limited to, spectroscopy and/or chromatography. If the monitoring technique includes spectroscopy, the spectroscopy can include mass, infrared, atomic emission, atomic absorption, nuclear magnetic resonance, Ramen, fluorescence, x-ray, atomic fluorescence, plasma emission, direct-current plasma, inductively-coupled plasma, laser induced breakdown, laser-induced plasma, microwave-induced plasma, spark and/or arc, UV, photoemission, force, dielectric, circular dichroism, rotational, vibrational, rigid rotor, EPR, spectral power distribution, metamerism, spectral reflectance, acoustic, dynamic mechanical, electron energy loss, and Auger electron, spectroscopies, and combinations of any two or more thereof. If the monitoring technique includes chromatography, the chromatography can include gas, liquid, ion-exchange, affinity, thin layer, supercritical fluid, and column, chromatographies, and combinations of any two or more thereof.

The method of the present invention can also include the step of introducing a catalyst into the reactor. In one embodiment, the catalyst can be introduced into the reactor at any point in the method. In one instance, if one or more catalysts are introduced, the one or more catalysts are introduced after the polymer feed material (or polymer starting material) is introduced into the reactor and as the polymer feed material (or polymer starting material) is decomposed. In another embodiment, the one or more catalysts are bound to one or more substrates or phase supports inside the reactor and the polymer feed material (or polymer starting material) is introduced over the one or more catalysts in a molten and/or gaseous form. With particular reference to FIG. 4, the catalyst 23 is applied on the impeller blade 22 of the assembly 20.

As is known in the art, catalysts can be used in two different ways. In general, the catalysts can effect the polymerization of olefins to polymers having high molecular weights and highly ordered structures. Conversely, the one or more catalysts can effect the reverse polymerization (i.e., the decomposition or unzipping of polymers) thereby catalyzing the break down of the polymers in the polymer feed material (or polymer starting material) into one or more monomers and break apart the highly ordered structures. In the process and system/apparatus of the present invention, one or more catalyst is used for reverse polymerization.

Under the effects of coupled electromagnetic induction field, the one or more polymers in the polymer feed material (or polymer starting material) is shown to depolymerize completely to its starting monomers. Added catalysts are present, in one embodiment, to react/catalyze the monomers in situ to generate value added functional monomers.

In one embodiment, it is possible and/or desirable to add water to the process/method of the present invention so as to facilitate the conversion of various double bond-containing of an alkene compounds to generate an alcohol, oxygen to generate an epoxide and further react/catalyze a compound to a diol or react with oxygen partially and alcohol to generate an acrylic monomer, all of which are commercially more valuable than the alkenes themselves.

Figure 8:
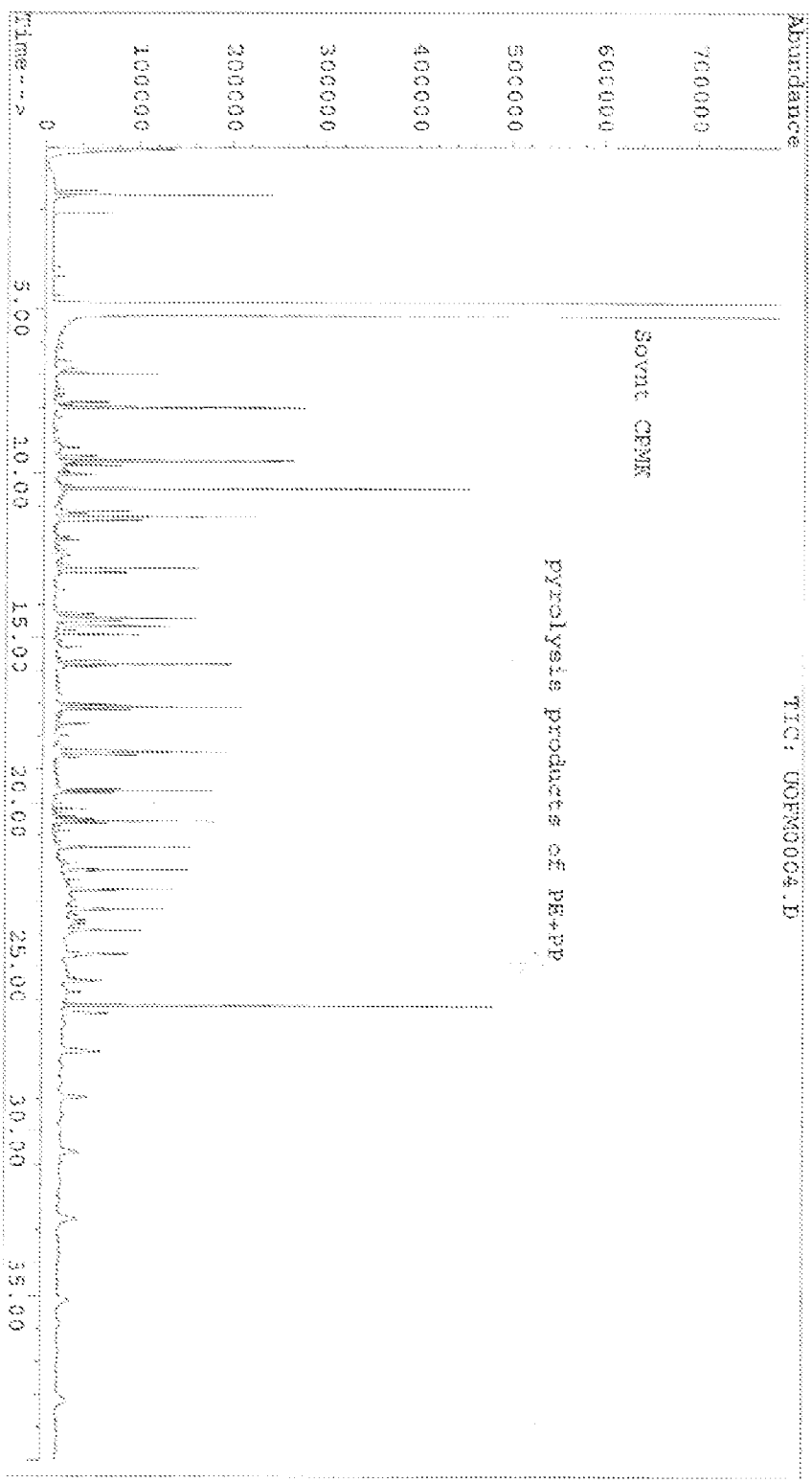
FIG. 8 is an exemplary result demonstrating harvesting of mixed monomers from mixed plastics in the presence of catalysts, according to the principles of the present teachings.

In another embodiment, the presence of one or more catalysts can influence the reaction pathway and the present invention yields products with a broader distribution (see FIG. 8). In these embodiments, the presence of one or more hydrogenation catalysts will lead to fuels with higher energy densities.

Non-limiting examples of such post transformational catalytic reactions are illustrated below:

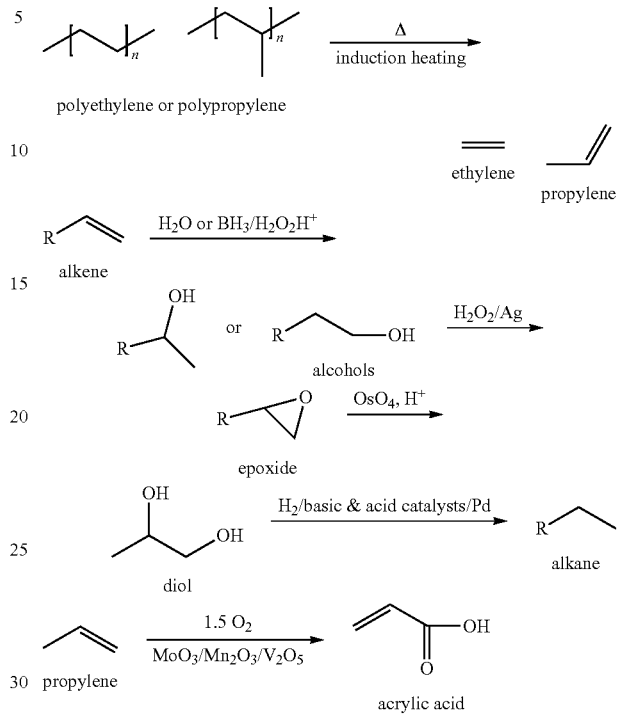

The one or more catalysts can be any catalysts known in the art. For example, in one embodiment the one or more catalysts can be chiral or achiral, can be symmetric or asymmetric, and/or can be homogeneous or heterogeneous. The one or more catalysts can also include any organic or inorganic moieties known in the art. In one embodiment, the one or more catalysts will facilitate, or catalyze, preferentially the reaction of one or more monomers initially formed by the depolymerization reaction of the present invention to obtain other value added compounds. In one embodiment, the one or more catalysts are present in an amount of less than or equal to about 500 parts per 100 parts by weight of the one or more polymer feed materials, or starting materials. In another embodiment, the one or more catalysts are present in an amount from about 0.1 part per one million parts by weight of the polymer feed material, or starting material, to about 100 parts of the catalyst per 100 parts by weight of the polymer feed material, or starting material. In still another embodiment, the one or more catalysts are present in an amount from about 0.1 part per one million parts by weight of the polymer feed material, or starting material, to about 20 parts of the one or more catalysts per 100 parts by weight of the polymer feed material, or starting material. Here, as well as elsewhere in the specification can claims, individual range values, or limits, can be combined to form additional and/or non-disclosed open and closed ranges.

For example, an alkene can be converted into an alcohol (primary or secondary) by addition of water across the double bonds, either catalyzed by acids or with hydroboration and reaction with hydrogen peroxide.

If one or more alkenes are reacted with hydrogen peroxide catalyzed by nano-structured silver they will be converted into epoxides in very high yields. These epoxides can further be reacted with one or more acids to form valuable esters, or reacted with water to form diols, or reacted under pressure with an acid, or base, catalyst to form polyols. These transformations are highly valuable in commodity products like foams, cosmetics etc.

In another embodiment, the present invention reacts one or more alkenes with osmium tetroxide or potassium permanganate to yield one or more diols directly. Again, diols are valuable chemicals used heavily in automotive and consumer products.

In still another embodiment, the present invention reacts propylene partially with 1.5 molecules of oxygen in presence of at least one molybdenum oxide catalyst to yield an acrylic acid monomer. As is known in the art, such compounds are very highly valuable intermediates in the coatings business and in the highly absorbent diaper industry.

In still another embodiment, the present invention reduces one or more double bonds with hydrogen as they are formed using catalysts like palladium, or one or more catalysts with customizable alkaline and/or acidic sites in the same molecule, to yield one or more saturated alkanes. Thus, in this embodiment it is possible to produce propane or butane from waste polypropylene or polybutylene polymers.

Specifically, the various catalysts including the aluminum and titanium oxides with varying ratios of acidity and alkalinity are formed and dispersed in nano-dimensional scale on the electromagnetic induction coupler.

Figure 9A:
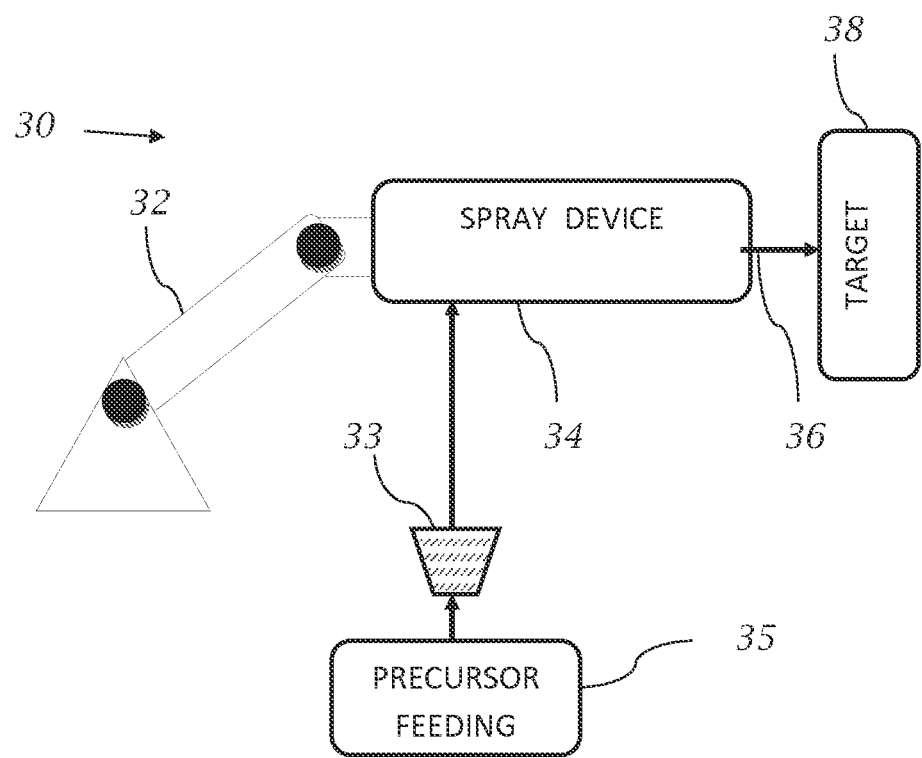
FIG. 9A a schematic view of an exemplary embodiment of the spray device for applying catalysts onto the impeller blades of FIG. 4.

With particular reference to FIG. 9A, one embodiment of the present invention is to apply the one or more catalysts using an appropriate fluid precursor which is injected to a hot gaseous stream for chemical/thermal treatment and consolidation into the desired catalyst layer on solid support. The fluid precursors upon injection into the hot gas pyrolyze in the stream resulting in fine molten/semi-molten/solid droplets of the desired materials that are consolidated into a film or particulate form.

The synthesis schemes of the present disclosure provide films possessing the desired morphological features, phase and compositions directly from chemical precursors, and thus, eliminate processing steps currently practiced in the industry. Further, the spray deposition techniques of the present invention enable the creation of geometrically complex coupler. In some embodiments, the use of fluid precursors where the component ingredients are in a completely dissolved state ensure homogeneity of component elements and enhance reaction rates compared to the solid state reactions commonly practiced in conventional processes, and thus can reduce the processing time.

As shown in FIG. 9A, a fabrication apparatus assembly 30 comprises a motion system 32 that mechanically commutes a spray device 34 to build a uniform film on a target 38, utilizing the fluid precursors from reservoir 35 in measured quantities via a pumping system 33. Apparatus assembly 30 can be installed in any environment.

Figure 9B:
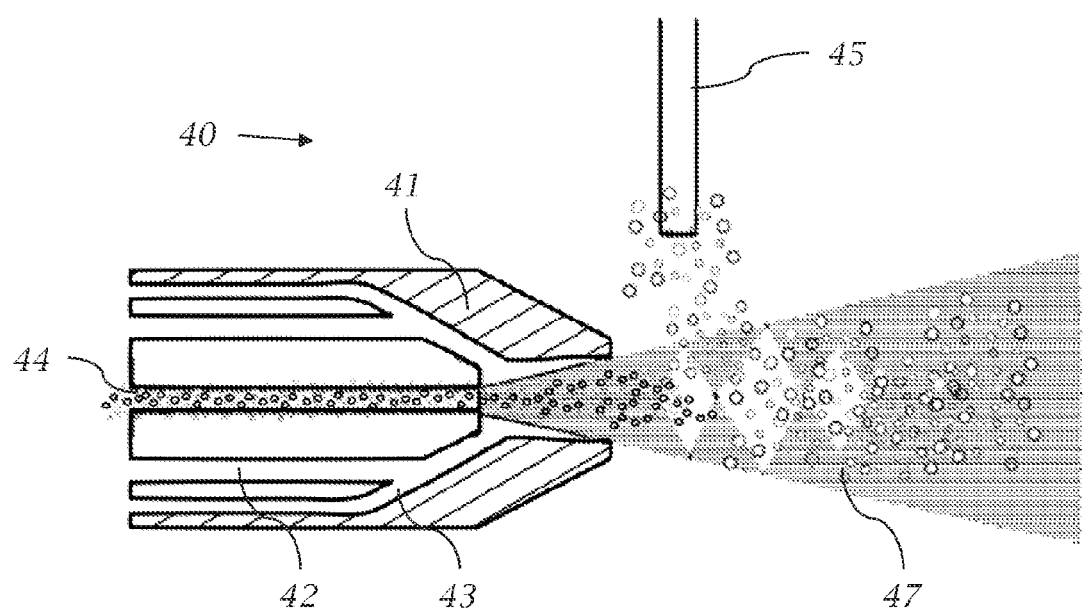
FIG. 9B is a schematic view of an exemplary embodiment of the spray device of FIG. 9A comprising a combustion flame system.

In some embodiments of spray device 40 a combustion flame is employed as illustrated in FIG. 9B. The combustion apparatus can employ a fuel such as hydrocarbon or hydrogen 42 as well as oxygen or air 43 to generate a sufficiently hot flame 47. The precursor material 44 can be injected to the flame axially via injector element 41 and/or radially via injector element 45 to synthesize the desired material and consolidate them into a deposit on target 38 according to the principles of the current teachings set forth herein. The chemical environment of the flame can be adjusted either to oxygen rich or oxygen lean by adjusting the fuel to air ratio. Such adjustments can control the chemistry of the target material.

Figure 9C:
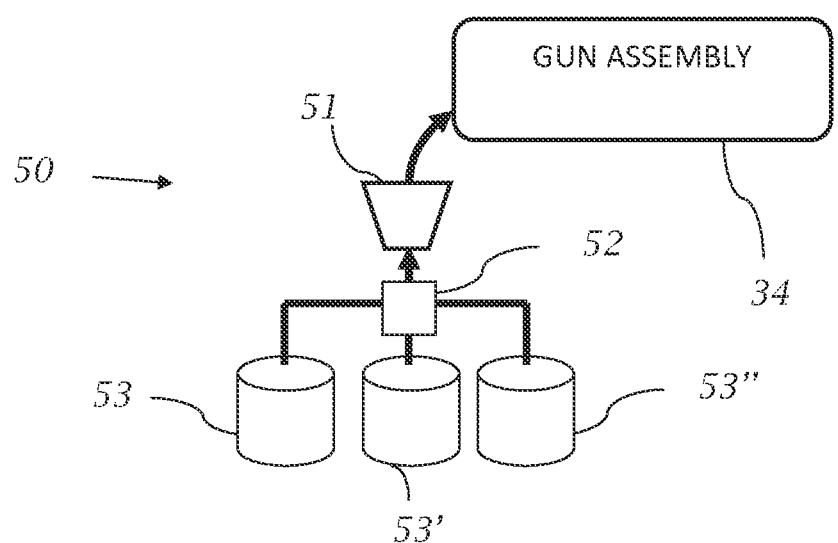
FIG. 9C is a schematic view of an exemplary embodiment of the precursor feed device of FIG. 9A comprising three liquid precursor reservoirs with a mixing and pumping system.

Referring to FIG. 9C, a precursor feed assembly 50 can comprise non-limiting precursor reservoirs 53, 53' and 53" feeding into a mixing chamber 52 which is pumped into the spray apparatus 34 via a mechanical pump 51.

Figure 9D:
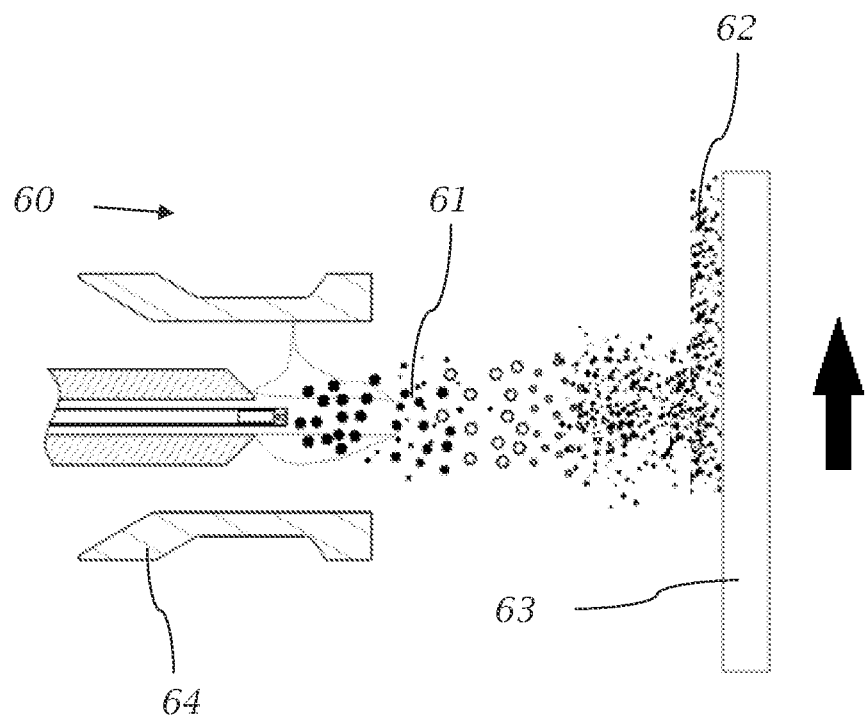
FIG. 9D is a schematic view of catalytic material film being deposited employing particles synthesized by plasma from liquid and/or gaseous precursors according to the principles of the present teachings.

FIG. 9D schematically illustrates a non-limiting embodiment of deposition scheme for a spray synthesized material 61 from a spray device 60 onto a target 63 forming a film 63. The spray device 64 can comprise a plasma device.

Direct achievement of films with desired chemistry, phase and morphology from solution precursors using spray apparatus as described here has unique attributes. The direct synthesis approach gives the ability to adjust the chemistry of the catalyst in flight and in situ. These teachings are not limited to the exemplary material systems discussed herein and can be employed to many other material systems.

An exemplary precursor for nanoscale $Al_2O_3$ particulate catalyst is aluminum nitrate $(Al(NO_3)_3.9H_2O)$ mixed 1:1 by weight in isopropyl alcohol. It should be noted that to achieve a pH adjusted solution, the addition of an acid or a base (dependent on the initial acidity or basicity) can be used. In some embodiments, the solution can be pH adjusted to achieve a homogeneous solution wherein the components contained there are completely dissolved in solution.

An exemplary precursor for titania is produced by mixing titanium isopropoxide with ethanol. Glacial acetic acid and hydrogen peroxide are used as dispersants.

Specifically, the aluminum and titanium oxides with varying ratios of acidity and alkalinity are formed by feeding respective precursors at varying ratios employing a feeding system illustrated in FIG. 9C.

Figure 10A:
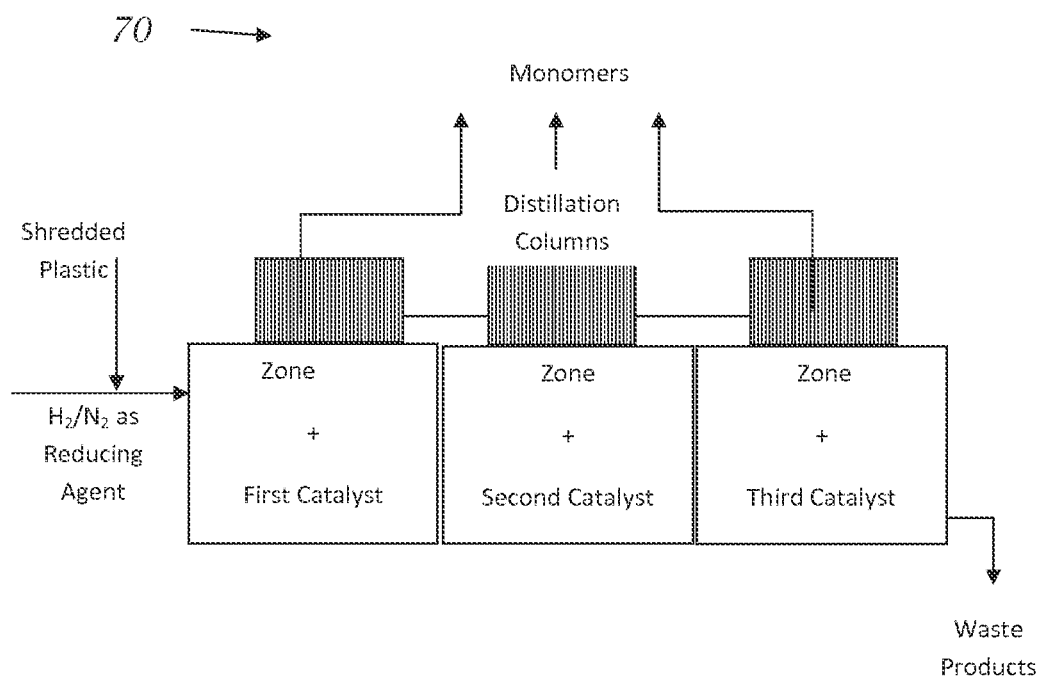
FIG. 10A is a block diagram illustrating an embodiment of the present invention comprising three customized catalyst zones.
Figure 10B:
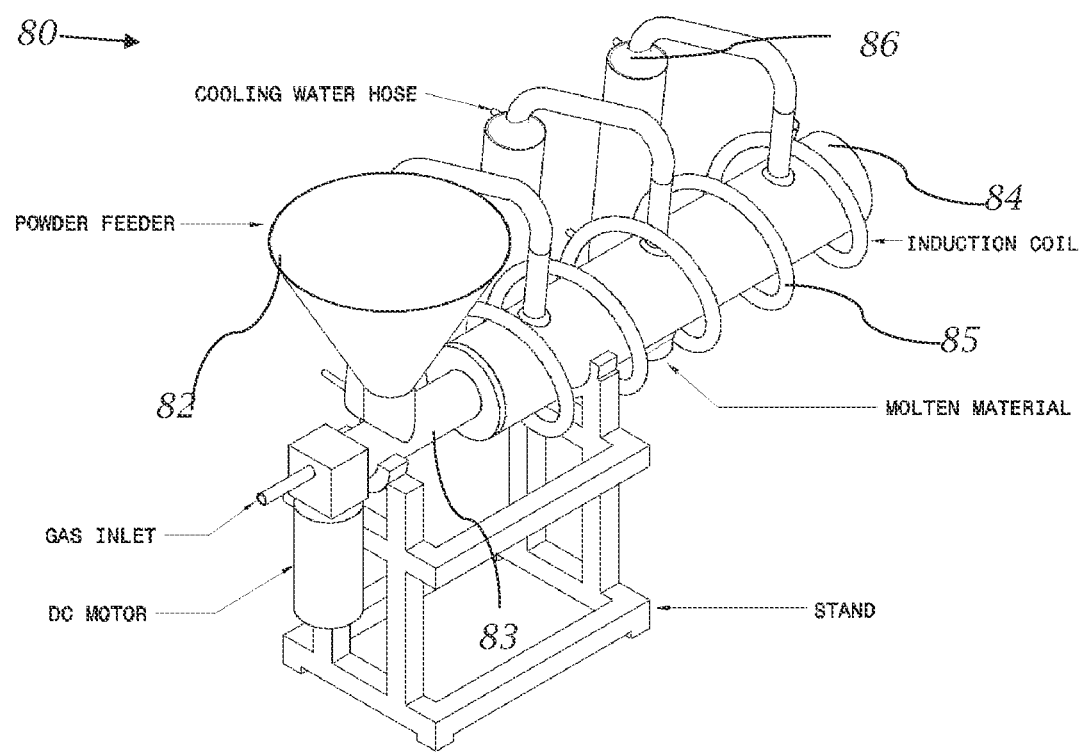
FIG. 10B is a schematic view of an exemplary embodiment of the present disclosure comprising the processing apparatus scheme of FIG. 10A with an induction coil.

With reference to FIGS. 10A and 10B, the one or more catalysts can be custom tailored and applied on the reactor assembly, progressively varying from acidic in nature to mixed to basic in nature via device 70 of FIG. 10A. According to one embodiment of the present invention, such customization provides for by-product selectivity as well as depolymerization efficiency.

More specifically, the one or more catalysts of the present invention can be custom tailored and applied on the electromagnetic induction coupler of the reactor assembly 80, for example, silver nanostructures, or nanoparticles, that in presence of oxygen can perform like osmium tetroxide made in situ. In one embodiment, such a catalyst could be nano-structured molybdenum designed to catalyze the partial oxidation of alkenes.

Figure 10C:
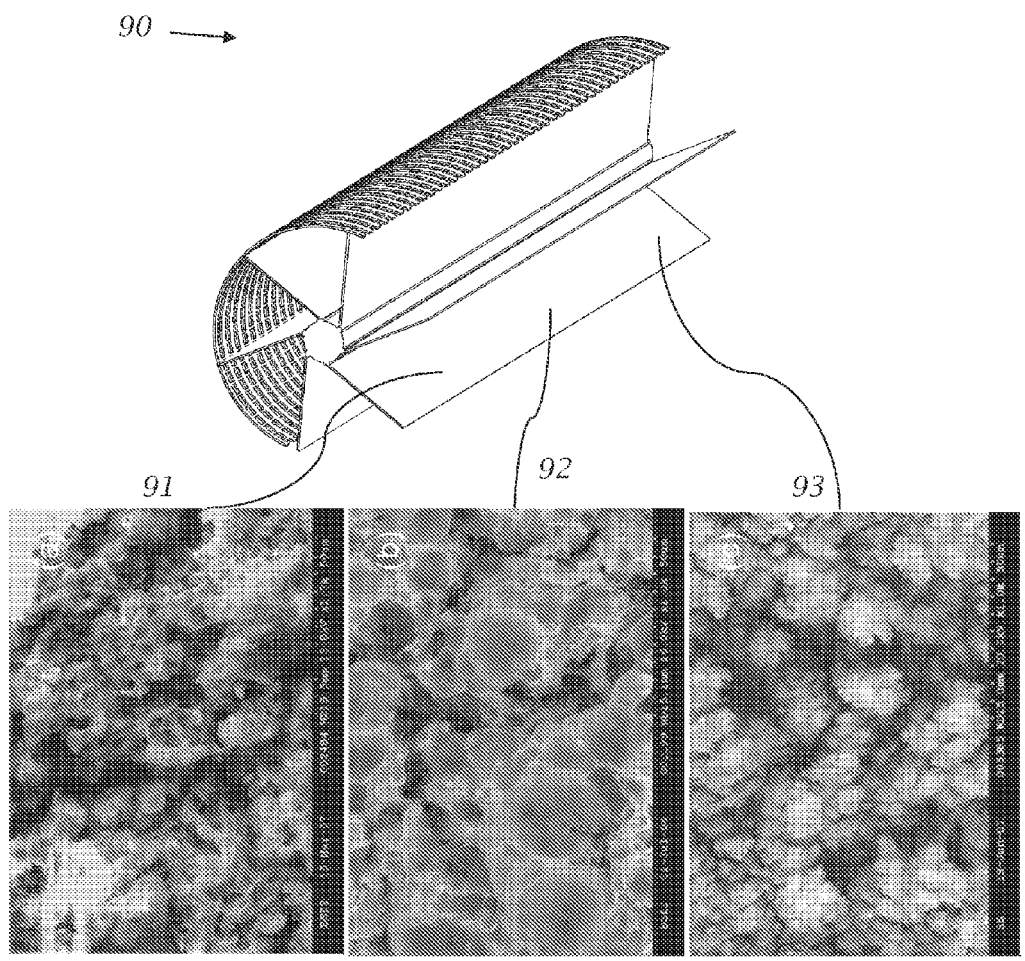
FIG. 10C is a schematic view of an impeller with graded catalysts according to the principles of the present teachings.

Further, it has been observed that a depolymerization reaction according to one embodiment of the present invention can be effected by nano-scale surfaces—the greatly increased area available for the reactants and products to bind, as well as the unique chemistry at the nano-scale open up a new vista in catalytic de-polymerization. As illustrated in FIG. 10C, such a nano-scale catalysts 91, 92, and/or 93 can in one embodiment be deposited on the electromagnetic induction coupler which could be a metal or non-metal or zeolite like structure 90. The material itself can be selected from elements like Si, Zr, Cu, Mg, Mn, etc., or oxides $SiO_2$, $Al_2O_3$, ZnO, MgO, BaO, $MnO_2$, $Fe_2O_3$ etc. These can be deposited by precursor plasma or combustion process according to the current teachings.

Figure 10D:
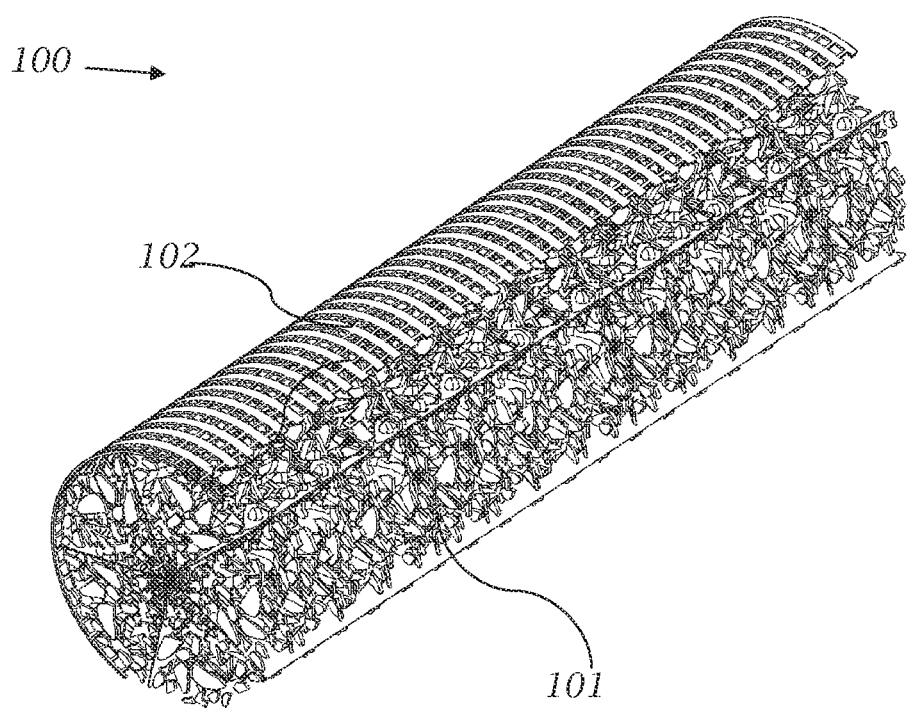
FIG. 10D is a schematic view of an impeller filled with zeolite pellets with graded catalysts of FIG. 10C according to the principles of the present teachings.

Further solid supported catalysts may be employed as illustrated in FIG. 10D. In assembly 100, the space between the electromagnetic induction coupler/impeller blades are filled with molecular sieves 101 and held in space by a cover screen 102.

Figure 11:
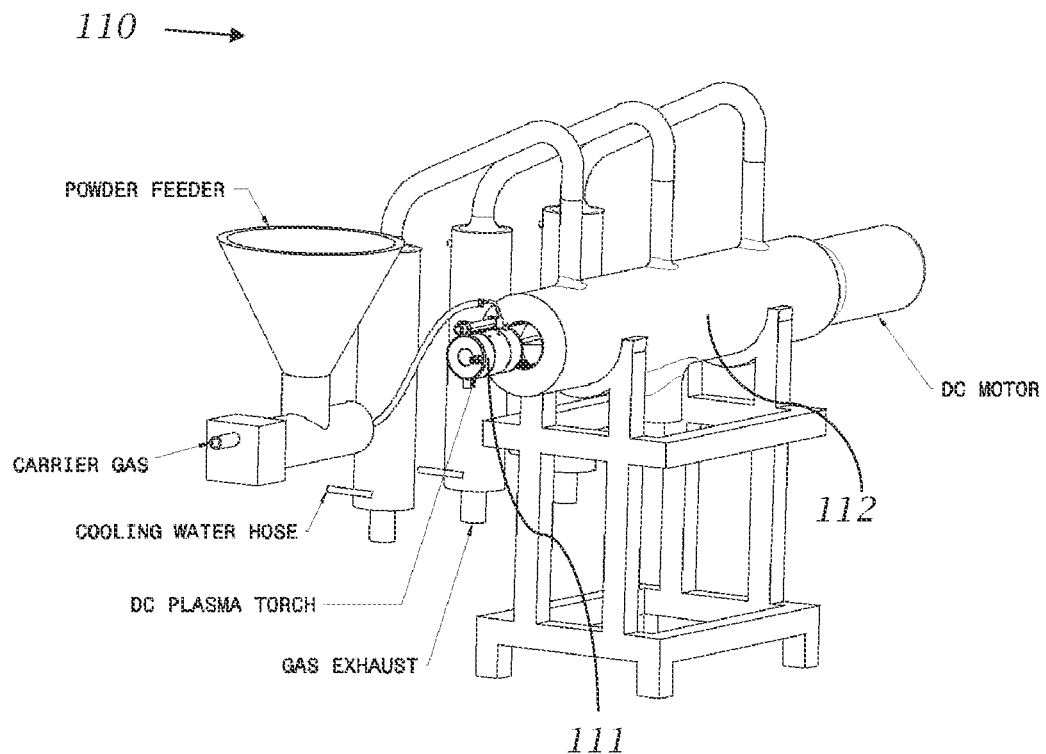
FIG. 11 is a perspective view of a system illustrating a plasma device being utilized to heat the plastic; and Corresponding reference numerals indicate corresponding parts throughout the several views of the drawings.

As illustrated in FIG. 11, in some embodiments of the present invention device 110 can employ a plasma device 111 to provide heat in addition to the electromagnetic induction field to depolymerize the polymer feed material, or starting material, present in chamber 112. The one or more catalysts can be added to the plasma device along with the polymer feed material, or starting material, or be supplied to the reactor assembly in accordance with various embodiments described above, or a combination approach can be employed.

In one embodiment, the present invention relates to a method of depolymerizing polymers, the method comprising the steps of: (i) providing one or more polymer starting materials, or feed materials; (ii) providing a reactor to depolymerize the one or more polymer starting materials, or feed materials, into one or more monomers; (iii) heating the one or more polymer starting materials, or feed materials, at a rate of from about 10° C./second to about 1000° C./second; and (iv) providing an electromagnetic induction field to facilitate the depolymerization of the one or more polymer starting materials, or feed materials, into their constituent monomers, wherein the method utilizes one or more catalysts that permit in situ reactions to yield one or more functional monomers.

In another embodiment, the present invention relates to a method of depolymerizing polymers, the method comprising the steps of: (a) providing one or more polymer starting materials, or feed materials; (b) providing a reactor to depolymerize the one or more polymer starting materials, or feed materials, into one or more monomers; (c) heating the one or more polymer starting materials, or feed materials, at a rate of from about 10° C./second to about 1000° C./second; (d) providing a coupled electromagnetic induction field to facilitate the depolymerization of the one or more polymer starting materials, or feed materials, into their constituent monomers; and (e) selectively harvesting at least one of the monomers produced by the method or converting at least one of the monomers into one or more stable value added products, wherein the method utilizes one or more catalysts that permit in situ reactions to yield one or more functional monomers.

In still another embodiment, the present invention relates to a method of depolymerizing polymers, the method comprising the steps of: (I) providing a polymer starting material, or feed material; (II) providing a reactor to depolymerize the polymer starting material, or feed material, into a constituent monomer (III) heating the one or more polymer starting materials, or feed materials, at a rate of from about 10° C./second to about 1000° C./second; and (IV) providing an coupled electromagnetic induction field to facilitate the depolymerization of the material, or feed material into its constituent monomer, wherein the method achieves a yield of constituent monomer of at least about 80 weight percent based on the extractable weight percent value contained in the polymer starting material, or feed material, subjected to depolymerization. In another embodiment, this method provides a yield of constituent monomer of at least about 82.5 weight percent, at least about 85 weight percent, at least about 87.5 weight percent, or even at least about 90 weight percent or higher based on the extractable weight percent value contained in polymer starting material. Here, as well as elsewhere in the specification can claims, individual range values, or limits, can be combined to form additional and/or non-disclosed open and closed ranges.

In still yet another embodiment, the present invention relates to a depolymerization method that utilizes one or more customized catalysts to permit and/or facilitate the yield of high fractions of value added desirable monomers from plastics whose base monomers are different. A non-limiting example of such a method of the present invention is obtaining a monomer AB from a mixture of two plastics (poly-A and poly-B) whose base monomers are A and B, respectively, or under certain conditions obtaining high fractions of monomer Y from a plastic (poly-X) whose base monomer is X.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:
1. A method of depolymerizing polymers, the method comprising the steps of:
   (i) providing one or more polymer starting materials or polymer feed materials;
   (ii) providing a reactor to depolymerize the one or more polymer starting materials or polymer feed materials into one or more monomers;
   (iii) heating the one or more polymer starting materials or polymer feed materials at a rate of from about 10° C./second to about 1000° C./second; and
   (iv) providing an electromagnetic induction field to facilitate the depolymerization of the one or more polymer starting materials or polymer feed materials into their constituent monomers, wherein the electromagnetic induction field is inductively coupled to a mixing portion of the reactor,
   wherein the method utilizes one or more catalysts that permit in situ reactions to yield one or more functional monomers.

2. The method according to claim 1, wherein the in situ reaction involves at least one catalytic composition supported on at least one solid substrate.

3. The method according to claim 1, wherein the method further comprises the step of:
(v) selectively harvesting at least one of the monomers produced by the method or converting at least one of the monomers into one or more stable value added products.

4. The method according to claim 1, wherein the reactor is provided with a plasma device in combination with the electromagnetic source to inductively couple with the mixing device and heat the one or more polymer starting materials or polymer feed materials to a desired temperature.

5. The method according to claim 1, wherein the one or more catalysts sites are alkaline in nature, acidic in nature, or a combination thereof.

6. The method according to claim 1, wherein the one or more catalysts are applied on one or more solid supports by an additive deposition process.

7. The method according to claim 1, wherein the one or more catalysts are synthesized on one or more solid supports by thermo-chemical processes.

8. The method according to claim 1, wherein the one or more catalysts are nanoscale catalysts.

9. The method according to claim 8, wherein the one or more nanoscale catalysts enhance the depolymerization process and perform additional chemical transformations to yield and/or obtain functional chemicals.

10. The method according to claim 1, wherein the one or more monomers produced by the method according to claim 1 are the basic components which were used to form the one or more polymer starting materials or polymer feed materials.

11. The method according to claim 1, wherein the method further comprises the step of: reacting one or more of the monomers to yield one or more functional chemicals.

12. The method according to claim 1, wherein the heating rate in Step (iii) is about 50° C./second to about 500° C./second.

13. The method according to claim 1, wherein the heating rate in Step (iii) is about 100° C./second to about 200° C./second.

14. The method according to claim 1, wherein the heating rate in Step (iii) is about 200° C./second.

15. A method of depolymerizing polymers, the method comprising the steps of:
(a) providing one or more polymer starting materials or polymer feed materials;
(b) providing a reactor to depolymerize the one or more polymer starting materials or polymer feed materials into one or more monomers;
(c) heating the one or more polymer starting materials or polymer feed materials at a rate of from about 10° C./second to about 1000° C./second;
(d) providing an electromagnetic induction field to facilitate the depolymerization of the one or more polymer starting materials or polymer feed materials into their constituent monomers, wherein the electromagnetic induction field is inductively coupled to a mixing portion of the reactor; and
(e) selectively harvesting at least one of the monomers produced by the method or converting at least one of the monomers into one or more stable value added products,
wherein the method utilizes one or more catalysts that permit in situ reactions to yield one or more functional monomers.

16. The method according to claim 15, wherein the in situ reaction involves at least one catalytic composition supported on at least one solid substrate.

17. The method according to claim 15, wherein the reactor is provided with a plasma device in combination with the electromagnetic source to inductively couple with the mixing device and heat one or more polymer starting materials or polymer feed materials to a desired temperature.

18. The method according to claim 15, wherein the one or more catalysts sites are alkaline in nature, acidic in nature, or a combination thereof.

19. The method according to claim 15, wherein the one or more catalysts are applied on one or more solid supports by an additive deposition process.

20. The method according to claim 15, wherein the one or more catalysts are synthesized on one or more solid supports by thermo-chemical processes.

21. The method according to claim 15, wherein the one or more catalysts are nanoscale catalysts.

22. The method according to claim 21, wherein the one or more nanoscale catalysts enhance the depolymerization process and perform additional chemical transformations to yield and/or obtain functional chemicals.

23. The method according to claim 15, wherein the one or more monomers produced by the method according to claim 15 are the basic components which were used to form the one or more polymer starting materials or polymer feed materials.

24. The method according to claim 15, wherein the method further comprises the step of: reacting one or more of the monomers to yield one or more functional chemicals.

25. The method according to claim 15, wherein the heating rate in Step (c) is about 50° C./second to about 500° C./second.

26. The method according to claim 15, wherein the heating rate in Step (c) is about 100° C./second to about 200° C./second.

27. The method according to claim 15, wherein the heating rate in Step (c) is about 200° C./second.

28. A method of depolymerizing polymers, the method comprising the steps of:
(I) providing a polymer starting material or polymer feed material;
(II) providing a reactor to depolymerize the polymer starting material or polymer feed material into a constituent monomer;
(III) heating the polymer starting material or polymer feed material at a rate of from about 10° C./second to about 1000° C./second; and
(IV) providing an electromagnetic induction field to facilitate the depolymerization of the polymer starting material or polymer feed material into its constituent monomer, wherein the electromagnetic induction field is inductively coupled to a mixing portion of the reactor,
wherein the method achieves a yield of constituent monomer of at least about 80 weight percent based on the extractable weight percent value contained in the polymer starting material or polymer feed material subjected to depolymerization.

29. The method according to claim 28, wherein the method utilizes one or more catalysts that permit in situ reactions to yield one or more functional monomers.

30. The method according to claim 29, wherein the in situ reaction involves at least one catalytic composition supported on at least one solid substrate.

31. The method according to claim 28, wherein the method further comprises the step of:
(V) selectively harvesting at least one of the monomers produced by the method or converting at least one of the monomers into one or more stable value added products.

32. The method according to claim 28, wherein the reactor is provided with a plasma device in combination with the electromagnetic source to inductively couple with the mixing device and heat the polymer starting material or polymer feed material to a desired temperature.

33. The method according to claim 29, wherein the one or more catalysts sites are alkaline in nature, acidic in nature, or a combination thereof.

34. The method according to claim 29, wherein the one or more catalysts are applied on one or more solid supports by an additive deposition process.

35. The method according to claim 29, wherein the one or more catalysts are synthesized on one or more solid supports by thermo-chemical processes.

36. The method according to claim 29, wherein the one or more catalysts are nanoscale catalysts.

37. The method according to claim 36, wherein the one or more nanoscale catalysts enhance the depolymerization process and perform additional chemical transformations to yield and/or obtain functional chemicals.

38. The method according to any of claim 28, wherein the one or more monomers produced by the method according to claim 28 are the basic components which were used to form the polymer starting material or polymer feed material.

39. The method according to claim 28, wherein the method further comprises the step of:
reacting one or more of the monomers to yield one or more functional chemicals.

40. The method according to claim 28, wherein the heating rate in Step (III) is about 50° C./second to about 500° C./second.

41. The method according to claim 28, wherein the heating rate in Step (III) is about 100° C./second to about 200° C./second.

42. The method according to any of claim 28, wherein the heating rate in Step (III) is about 200° C./second.

43. The method of claim 1, wherein the one or more catalysts are selected from osmium tetroxide, potassium permanganate, one or more molybdenum oxide catalysts in combination with oxygen, one or more palladium catalysts, one or more catalysts with alkaline and/or acidic sites in the same molecule, one or more catalysts designed to reduce one or more double bonds in the presence of hydrogen to yield one or more saturated alkanes, one or more aluminum oxides, one or more titanium oxides, one or more Si catalysts, one or more Zr catalysts, one or more Cu catalysts, one or more Mg catalysts, one or more Mn catalysts, or combinations of any two or more thereof.

44. The method of claim 15, wherein the one or more catalysts are selected from osmium tetroxide, potassium permanganate, one or more molybdenum oxide catalysts in combination with oxygen, one or more palladium catalysts, one or more catalysts with alkaline and/or acidic sites in the same molecule, one or more catalysts designed to reduce one or more double bonds in the presence of hydrogen to yield one or more saturated alkanes, one or more aluminum oxides, one or more titanium oxides, one or more Si catalysts, one or more Zr catalysts, one or more Cu catalysts, one or more Mg catalysts, one or more Mn catalysts, or combinations of any two or more thereof.

45. The method of claim 29, wherein the one or more catalysts are selected from osmium tetroxide, potassium permanganate, one or more molybdenum oxide catalysts in combination with oxygen, one or more palladium catalysts, one or more catalysts with alkaline and/or acidic sites in the same molecule, one or more catalysts designed to reduce one or more double bonds in the presence of hydrogen to yield one or more saturated alkanes, one or more aluminum oxides, one or more titanium oxides, one or more Si catalysts, one or more Zr catalysts, one or more Cu catalysts, one or more Mg catalysts, one or more Mn catalysts, or combinations of any two or more thereof.

46. The method of claim 30, wherein the at least one catalytic composition is selected from one or more of osmium tetroxide, potassium permanganate, one or more molybdenum oxide catalysts in combination with oxygen, one or more palladium catalysts, one or more catalysts with alkaline and/or acidic sites in the same molecule, one or more catalysts designed to reduce one or more double bonds in the presence of hydrogen to yield one or more saturated alkanes, one or more aluminum oxides, one or more titanium oxides, one or more Si catalysts, one or more Zr catalysts, one or more Cu catalysts, one or more Mg catalysts, one or more Mn catalysts, or combinations of any two or more thereof.

* * * * *

UNITED STATES PATENT AND TRADEMARK OFFICE
CERTIFICATE OF CORRECTION

| | | |
|---|---|---|
| PATENT NO. | : 9,505,901 B2 | |
| APPLICATION NO. | : 13/992617 | |
| DATED | : November 29, 2016 | |
| INVENTOR(S) | : Pravansu S. Mohanty and Swaminathan Ramesh | |

It is certified that error appears in the above-identified patent and that said Letters Patent is hereby corrected as shown below:

Page 2 of the published patent should be corrected as follows:

(56) References Cited
FOREIGN PATENT DOCUMENTS

"WO2006094421A1" should be correct to "WO2006098421A1"

Signed and Sealed this
Sixth Day of June, 2017

Michelle K. Lee
*Director of the United States Patent and Trademark Office*